United States Patent
Olson et al.

(10) Patent No.: US 10,238,536 B2
(45) Date of Patent: Mar. 26, 2019

(54) OCULAR FILTRATION DEVICES, SYSTEMS AND METHODS

(71) Applicant: THE REGENTS OF THE UNIVERSITY OF COLORADO, A BODY CORPORATE, Denver, CO (US)

(72) Inventors: Jeffrey Olson, Denver, CO (US); Ramanath Bhandari, Springfield, IL (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 262 days.

(21) Appl. No.: 14/435,407

(22) PCT Filed: Oct. 11, 2013

(86) PCT No.: PCT/US2013/064473
§ 371 (c)(1),
(2) Date: Apr. 13, 2015

(87) PCT Pub. No.: WO2014/059233
PCT Pub. Date: Apr. 17, 2014

(65) Prior Publication Data
US 2015/0265469 A1    Sep. 24, 2015

Related U.S. Application Data

(60) Provisional application No. 61/712,511, filed on Oct. 11, 2012, provisional application No. 61/769,443, filed on Feb. 26, 2013.

(51) Int. Cl.
*A61F 9/007* (2006.01)
*A61M 1/00* (2006.01)

(52) U.S. Cl.
CPC ......... *A61F 9/00781* (2013.01); *A61M 1/008* (2013.01); *A61M 2210/0612* (2013.01)

(58) Field of Classification Search
CPC ............... A61F 9/00781; A61M 1/008; A61M 2210/0612
See application file for complete search history.

(56) References Cited

U.S. PATENT DOCUMENTS

| 5,626,558 A | 5/1997 | Suson |
| 2003/0236483 A1 | 12/2003 | Ren |

(Continued)

FOREIGN PATENT DOCUMENTS

| EP | 2034937 | 3/2009 |
| WO | 2007087061 | 8/2007 |

(Continued)

OTHER PUBLICATIONS

International Search Report for International (PCT) Patent Application No. PCT/US2013/064473, dated Jan. 8, 2014, 4 pages.

(Continued)

*Primary Examiner* — Leslie Deak
(74) *Attorney, Agent, or Firm* — Snell & Wilmer L.L.P.

(57) ABSTRACT

A glaucoma drainage device regulator (GDDR) is disclosed which comprises a membrane and a lumen to regulate the flow of aqueous in conjunction with different ocular (e.g., glaucoma) filtering procedures. In connection with aqueous shunting, the GDDR can be placed over the tip of a shunt tube in the anterior chamber, either at the time of initial surgery or also in devices which have been previously implanted. In connection with trabeculectomy, the GDDR can comprise a flange for seating the GDDR at the sclerostomy in trabeculectomy surgery.

20 Claims, 6 Drawing Sheets

(56) References Cited

U.S. PATENT DOCUMENTS

| | | |
|---|---|---|
| 2004/0162545 A1 | 8/2004 | Brown |
| 2004/0254517 A1 | 12/2004 | Quiroz-Mercado et al. |
| 2006/0069340 A1 | 3/2006 | Simon |
| 2010/0168644 A1 | 7/2010 | Brown |
| 2012/0035525 A1 | 2/2012 | Silvestrini |
| 2012/0089073 A1 | 4/2012 | Cunningham, Jr. |
| 2013/0267887 A1* | 10/2013 | Kahook .............. A61F 9/00781 604/9 |

FOREIGN PATENT DOCUMENTS

| | | |
|---|---|---|
| WO | 2012040380 | 3/2012 |
| WO | 2014059233 | 4/2014 |

OTHER PUBLICATIONS

Written Opinion for International (PCT) Patent Application No. PCT/US2013/064473, dated Jan. 8, 2014, 7 pages.

International Preliminary Report on Patentability for International (PCT) Patent Application No. PCT/US2013/064473, dated Jan. 8, 2014, 8 pages.

European Search Report and Supplementary European Search Report in the European Patent Application No. 13846189, dated Jun. 8, 2016.

Office Action in the European Patent Application No. 13846189, dated Aug. 7, 2017.

* cited by examiner

OCULAR FILTRATION DEVICES, SYSTEMS AND METHODS

BACKGROUND

Field

The present disclosure relates to ocular filtration devices, systems and methods, and more particularly, to glaucoma treatment devices, systems and methods.

Discussion of the Related Art

Glaucoma is a rapidly growing problem in the industrialized world and presents a leading cause of vision loss and blindness. Currently, glaucoma is the second leading cause of irreversible blindness. Glaucoma prevalence is currently approximately 2.2 million people in the United States and over 60 million worldwide. Despite recent technological and pharmacologic advances in medicine, the number of people losing sight due to glaucoma continues to increase.

In brief, glaucoma is characterized by high intraocular pressures, which over time cause damage to the optic nerve, resulting in loss of peripheral vision in early cases. Later stage disease can lead to loss of central vision and permanent blindness. Treatment is aimed at lowering intraocular pressure.

The current standard of care for treating the blinding complications of glaucoma revolves around topical medications, laser treatments, and surgery for the most advanced cases, all aimed at lowering intraocular pressure. For patients with advanced disease, filtering surgery (e.g., aqueous shunting or trabeculectomy) is often required to prevent vision loss.

With respect to aqueous shunting, implanted glaucoma drainage devices (GDDs) are typically used to create an alternate aqueous pathway from the anterior chamber by shunting aqueous out of the eye through a tube to a sub-conjunctival bleb or reservoir which is usually connected to a plate under the conjunctiva. A major disadvantage of this surgery is that the aqueous may tend to flow too rapidly out of the tube until a fibrous membrane has encapsulated the reservoir. To this end, medical practitioners may elect to tie off the external portion of the tube or block its lumen with suture or other material, such that once the reservoir has become encapsulated, the suture can be removed. These represent an all-or nothing option with regards to the amount of aqueous flow. Further, some GDDs have a valve which theoretically prevents flow below certain pressures, but cannot be titrated or adjusted by the medical practitioner.

As with conventional GDD implantation, current trabeculectomy surgeries are not titratable by the medical practitioner post-operatively. During surgery, viscoelastic substances may be left in the anterior chamber to slow the rate of aqueous filtration for the first 24-48 hours, or contact lenses placed on the surface of the eye post-operatively to prevent low pressures. Alternatively, the medical practitioner may place sutures over the sclerostomy flap, and can open these with a laser or mechanically. Again, these allow the medical practitioner to either prevent or allow flow, but without precision, often leading to gross under- or over-filtration. This problem contributes to the high rate of surgical failure with these surgeries long-term.

At least in part due to not being titratable, current surgical techniques are plagued by high rates of complications (such as overfiltering and underfiltering, hypotony, choroidal effusions/hemorrhages), with a failure rate of 50% at 5 years. To address this issue, there exist prior art of using biodegradable implants, fibroblast inhibitors, anti-metabolites, and other drugs over the surface of the scleral flap or stainless steel shunts under the scleral flap to encourage continued flow. For example, the Ex-Press Mini Glaucoma Shunt was originally developed by Optonol, Ltd. (Neve Ilan, Israel) for implantation under the conjunctiva for controlling intraocular pressure (IOP). This biocompatible device is almost 3 mm long with an external diameter of approximately 400 microns. It is a non-valved, MRI compatible, stainless steel device with a 50 micron lumen. It has an external disc at one end and a spur-like extension on the other to prevent extrusion.

SUMMARY

A glaucoma drainage device regulator (GDDR) is disclosed which comprises a membrane and a lumen to regulate the flow of aqueous in conjunction with different ocular (e.g., glaucoma) filtering procedures. In connection with aqueous shunting, the GDDR can be placed over the tip of a shunt tube in the anterior chamber, either at the time of initial surgery or also in devices which have been previously implanted. In connection with trabeculectomy, the GDDR can comprise a flange for seating the GDDR at the sclerostomy in trabeculectomy surgery.

In example embodiments of the present disclosure, a glaucoma drainage device regulator is described, comprising a membrane coupled with a lumen, wherein perforations in the membrane increase aqueous flow to lower intraocular pressure, and wherein the membrane is configured to be selectively perforated by a targeted energy source.

In other example embodiments of the present disclosure, a glaucoma drainage device regulator system is described, comprising a membrane, a lumen coupled with the membrane, a shunt tube coupled with the lumen, and a reservoir coupled with the shunt tube. In such example embodiments, perforations in the membrane increase aqueous flow to lower intraocular pressure, the glaucoma drainage device regulator system is used in connection with aqueous shunting, and the membrane is configured to be selectively perforated by photodisruptive or ablative laser.

In yet other example embodiments of the present disclosure, a method for lowering intraocular pressure is described, comprising implanting a membrane within a pathway for aqueous flow from an anterior chamber. In such example embodiments, the membrane is coupled with a lumen, perforations in the membrane increase aqueous flow to lower intraocular pressure within the anterior chamber, and the membrane is configured to be selectively perforated by a targeted energy source.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, in which like numerals denote like elements and.

DETAILED DESCRIPTION OF THE ILLUSTRATED EMBODIMENTS

Figure 1:
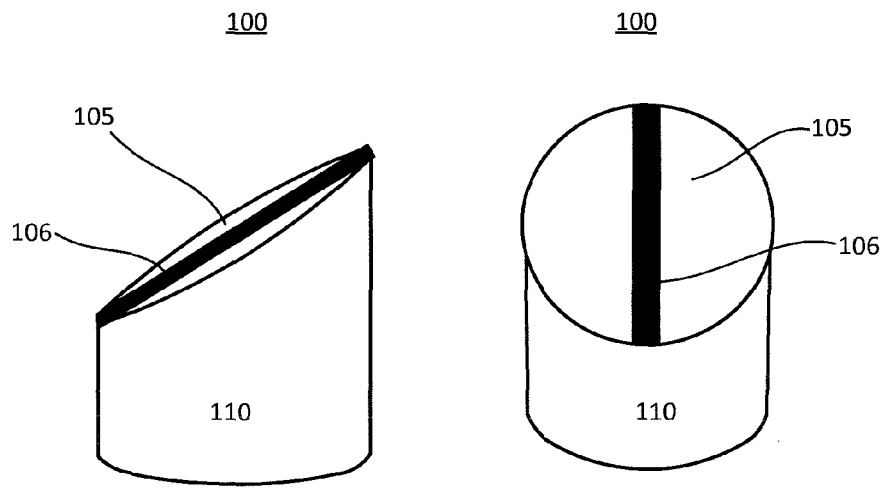
FIG. 1 illustrates views of an example GDDR in accordance with the present disclosure.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure can be described in connection with various principles and beliefs, the present disclosure should not be bound by theory.

As noted above, the flow rate of prior art devices cannot be accurately controlled or adjusted once implanted to fit the needs of the patient. What is therefore needed is a device which could allow the medical practitioner to precisely control the filtration flow rate months to years after surgery, decreasing surgical complications and improving patient outcomes.

The present disclosure obviates these drawbacks and others by allowing medical practitioners to post-operatively control the rate of flow through the device, allowing better, customized treatment for patients. The rate of flow through a tube can be expressed by Poiseuille's law, which states that flow is proportional to the radius raised to the fourth power. Consequently, small changes in the radius of the tube produce large changes in flow.

In an example embodiment, a glaucoma drainage device regulator (GDDR) comprises a membrane coupled with a lumen. In an example embodiment, the GDDR further comprises a flange. The GDDR is configured to be implanted in an eye to regulate aqueous flow from the anterior chamber and/or to lower intraocular pressure. In an example embodiment, the membrane is configured with perforations. In another example embodiment, the membrane is configured to be perforated post implantation, perhaps long after implantation. The perforations are configured, in an example embodiment, to increase the flow of aqueous from the anterior chamber and/or to lower intraocular pressure in a controllably adjustable manner. The lumen can, in an example embodiment, be coupled to the end of a shunt tube and/or reservoir.

With reference to FIG. 1, a GDDR 100 is disclosed which uses a membrane 105 to regulate the flow of aqueous in conjunction with different ocular (e.g., glaucoma) filtering procedures. Membrane 105 of GDDR 100 can be comprised of one or more biocompatible materials such as PVDF, silicone, filtration and nanofiltration membranes, nucleopore membranes, PMMA, dialysis membranes, cellulose, acrylic, fluorinated ethylene propylene, shape memory polymers, non-reactive polymers, collamers, nylon, and the like. Thus, in example embodiments, membrane 105 is implantable. Membrane 105 can be configured such that it allows no aqueous flow prior to perforation, or it may be permeable to low amounts of aqueous flow prior to perforation.

In example embodiments, a surface of membrane 105 can be color coded, numbered, or have writing or another target to indicate one or more areas to perforate in order to achieve a certain amount of flow, or to access different drainage areas, tubes, and/or shunts.

In some embodiments, per the medical practitioner's discretion, a targeted energy source can be used either directly or with the use of a mirrored lens to pass through overlying tissue and create small perforations or ruptures in the surface of membrane 105, thereby allowing the passage of aqueous. As used herein, "targeted energy source" refers to any energy source capable of creating small perforations or ruptures in the surface of membrane 105 without damaging the overlying or surrounding tissue, or in an otherwise non-invasive or minimally invasive manner. In example embodiments, a targeted energy source can be acoustic (e.g., ultrasound), thermal, photodisruptive or ablastive laser (Nd:Yag, argon, PASCAL, etc.). In other embodiments, membrane 105 can be perforated mechanically such as with a needle, scalpel or other sharp instrument.

In another example embodiment, membrane 105 can be configured to dissolve or be dissolved to facilitate increased passage of aqueous. in one example embodiment, membrane 105 can partially dissolve to increase the flow of aqueous or reduce intraocular pressure. In another example, specific portions of membrane 105 may fully dissolve to increase the flow of aqueous or reduce intraocular pressure. Biodegradable materials such as collagen can be used to this end.

A perforation can comprise a hole, a slit, or any physical change to membrane 105 that facilitates increased aqueous flow through membrane 105 and/or lowering intraocular pressure. In an example embodiment, any suitable number of perforations can be made in membrane 105. In an example embodiment, the perforations can be any suitable size or shape. Perforations can be created in any number of patterns to regulate the flow of aqueous. In an example embodiment, membrane 105 is configured to be perforated by the medical practitioner so that an increase in the number of perforations facilitates an increase in the rate of flow, allowing a titration of aqueous flow based on the clinical need.

In an example embodiment, membrane 105 comprises dividers 106. Dividers 106 are configured to allow the medical practitioner to perforate specific areas selectively (e.g., dividers 106 that correspond to a plurality of lumens, or multi-lumen or bifurcated lumens in connection with aqueous shunting). In another example embodiment, membrane 105 may comprise a continuous face. In this example embodiment, the medical practitioner can still perforate specific areas selectively to further reduce intraocular pressure, as desired. Membrane 105 can be configured as a cap to one or more lumens in connection with aqueous shunting.

Membrane 105 can be impregnated with medicants, such as steroids or others that inhibit fibroblast proliferation, or anti-glaucoma medicants, that are released upon perforation.

In the alternative, or in addition, these same medicants can be sequestered behind membrane 105 and be configured to be released upon perforation.

With continued reference to FIG. 1, GDDR 100 further comprises a lumen 110. Lumen 110 of GDDR 100 can be comprised of one or more biocompatible materials such as silicone, acrylic, PMMA, fluorinated ethylene propylene, stainless surgical steel, shape memory polymers, collamers, PVDF, and the like.

In various embodiments, membrane 105 is angled relative to lumen 110. For example, membrane 105 can be configured to be angled relative to the longitudinal axis of lumen 110 at about 30 to about 60 degrees, or at about 45 degrees. Moreover, membrane 105 can be configured to be angled relative to the longitudinal axis of lumen 110 at any suitable angle, including a perpendicular configuration at 0 degrees. In one example embodiment, the angle is selected to increase the surface area of membrane 105. In another example embodiment, the angle is selected to facilitate perforating membrane 105. The angle can allow the surgeon easier surgical access to the face of membrane 105 in order to use a laser or other device to create perforations.

Figure 2:
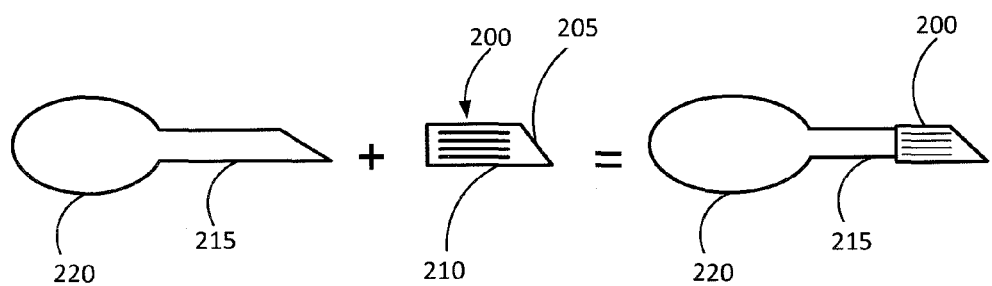
FIG. 2 illustrates exploded and coupled views of a GDDR, a shunt tube, and a reservoir in accordance with an example embodiment of the present disclosure.

Turning now to FIG. 2, in connection with various embodiments, a lumen 210 of a GDDR 200 can be placed over the tip of a shunt tube 215 in the anterior chamber, either at the time of initial surgery or also in devices which have been previously implanted. In this regard, lumen 210 can be generally configured to sealingly couple with one or more shunt tubes 215. In example embodiments, one or more shunt tubes 215 can be part of conventional glaucoma drainage devices so as to retrofit or be an accessory to the same.

In other example embodiments, lumen 210 can be placed over "minimally-invasive glaucoma devices" or MIGS, for example, a micro-bypass stent (iStent inject, Glaukos Corporation, Laguna Hills, Calif., USA), a canalicular scaffold (Hydrus, Ivantis Inc., Irvine, Calif., USA), or an ab interno suprachoroidal microstent (CyPass, Transcend Medical, Menlo Park, Calif., USA). Further, GDDR 200 can be placed onto various devices, or incorporated into their design as a single piece. By so doing, the lumens of the devices can be made larger, with an exponential rise in the potential flow that can be accessed at a later date through laser or mechanical disruption of the flow regulating membrane. Further, multiple devices with GDDR 200 in place may be placed during one surgical setting, so that some are covered with GDDR 200 and hence the flow restricted until such time that the flow is needed. Alternatively, multi-lumen shunts can be incorporated into devices which drain into Schlem's canal, the subconjunctival space, and the suprachoroidal space, with the GDDR covered the lumens. As further reduction in intraocular pressure is required, the covered lumens 210 can be accessed with laser to perforate the flow restricting membrane.

Lumen 210 can be further generally configured to maintain aqueous flow with the shunt tube(s) 215. In this regard, the present disclosure can comprise a plurality of lumens 210, or multi-lumen or bifurcated lumens 210. In various embodiments, a plurality of separate lumens 210 are configured to sealingly engage with a plurality of separate shunt tubes 215.

Moreover, whether in connection with an initial surgery (e.g., as an integrated system) or for use with devices which have been previously implanted, illustrative aqueous shunting systems in accordance with the present disclosure can comprise one or more shunt tubes 215 and/or reservoirs 220 to receive the flow of aqueous. In an example embodiment, shunt tube 215 can have an outer diameter of approximately 0.635 mm (23 g), and an inner diameter of approximately 0.31 mm (30 g). Moreover, any suitable inner/outer diameter shunt tube may be used. Notwithstanding the foregoing, in various embodiments, the present disclosure provides systems comprising one or more shunt tubes 215 having smaller or larger diameters than those taught in the prior art, or multi-lumen or bifurcated shunt tubes 215. By way of non-limiting example, a larger diameter, for example 20 gauge or 18 gauge or greater, shunt tube 215 (or a multi-lumen or bifurcated shunt tube 215) can be configured to allow for greater aqueous flow months or years after surgical implantation (e.g., when the patient's disease worsens) in cases where the high aqueous flow immediately post-operatively would be prohibitive. In this regard, one or more shunt tubes 215 having smaller or larger diameters than those taught in the prior art, or multi-lumen or bifurcated shunt tubes 215 can be implanted, and membrane 205 of GDDR 200 subsequently perforated as needed to increase the flow of aqueous into the one or more shunt tubes 215 and/or reservoirs 220.

Stated another way, in an example embodiment, the inner diameter of shunt tube 215 can be configured to be greater than the maximum diameter that could be used on a patient at the time of operation if the operation was performed without the membrane of the present disclosure. Without membrane 205 of the present disclosure, a shunt tube with too great an inner diameter, a multi-lumen or bifurcated shunt tube, or a plurality of shunt tubes, as taught by the present disclosure, would allow too much flow. In contrast, with GDDR 200 of the present disclosure, the inner diameter of shunt tube 215 is greater than the maximum diameter that could be used on a patient at the time of operation because the flow is restricted by membrane 205 in addition to the inner diameter of shunt tube 215. Moreover, the same shunt tube 215 can continue to be used at a subsequent time when additional perforation increases the flow of aqueous. Thus, subsequent adjustments can be made with minimal surgery impact on the patient. In like manner, the present disclosure provides for a multi-lumen or bifurcated shunt tube, a plurality of shunt tubes, and a plurality of reservoirs, whereas the prior art would render such designs prohibitive due to the inability to prevent too much flow.

Figure 3A:
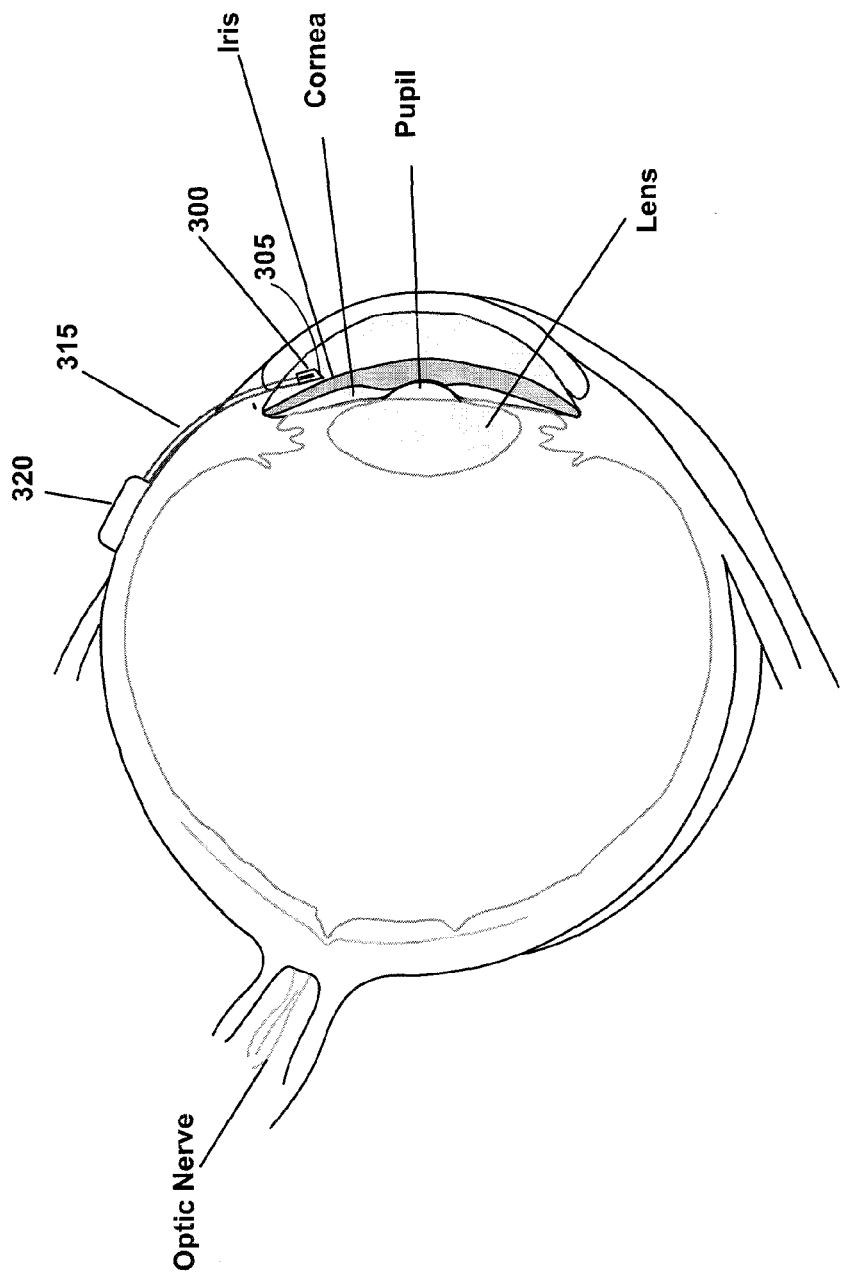
FIG. 3A illustrates an example GDDR system in accordance with the present disclosure implanted in connection with aqueous shunting.

FIG. 3A illustrates an example GDDR 300 in accordance with the present disclosure implanted in connection with aqueous shunting. In an example embodiment, a membrane 305 of GDDR 300 is angled to face the cornea, and thereby allow the surgeon easier surgical access to the face of membrane 305 in order to use a laser or other device to create perforations. GDDR 300 can be like a small cap that can be applied to (or removed from) any existing GDD tube 315 and/or reservoir 320.

In an example embodiment, GDDR 300 may be particularly useful for cases of glaucoma shunt tubes 315 and/or reservoirs 320, including ahmed, malteno, and krupin devices, as well as both fornix and limbus based trabeculectomy procedures.

Figure 3B:
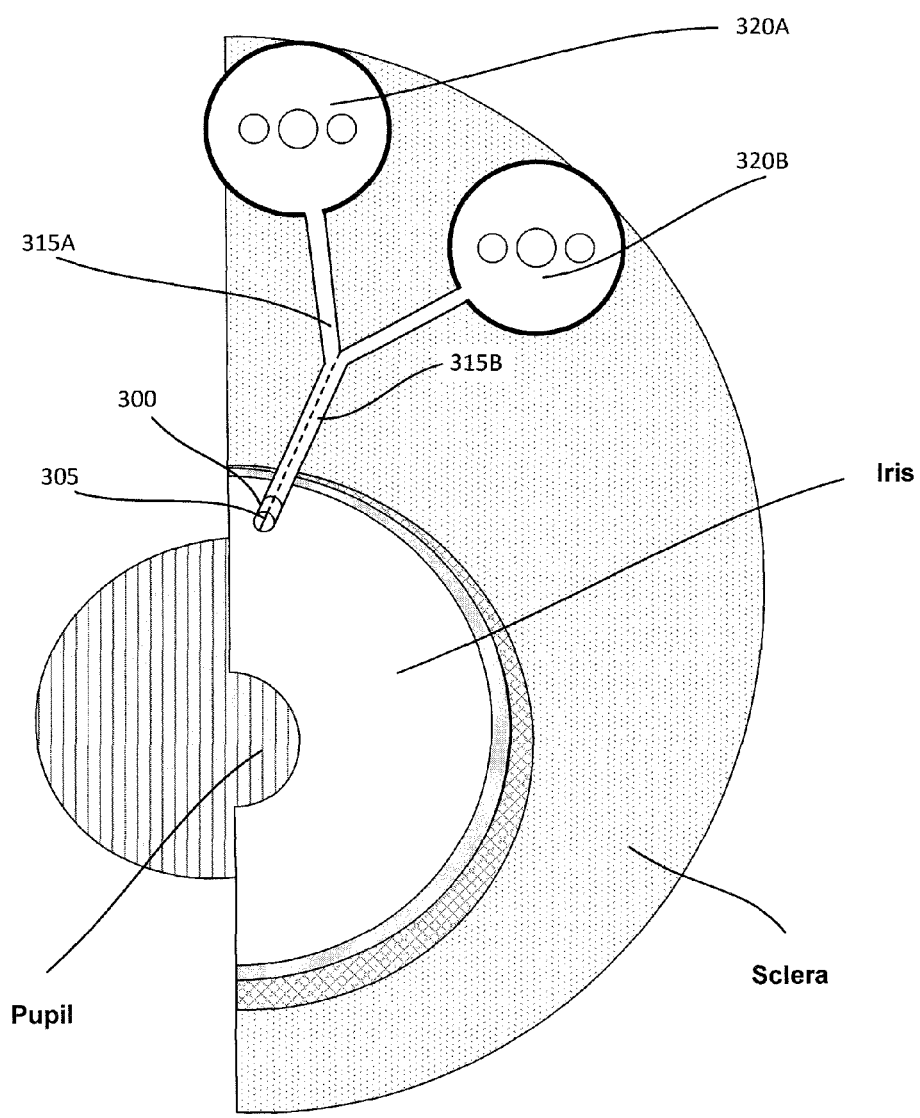
FIG. 3B illustrates another example GDDR system in accordance with the present disclosure implanted in connection with aqueous shunting and a multi-lumen or bifurcated shunt tube.

With reference to FIG. 3B, and as noted above, the present disclosure provides for a multi-lumen or bifurcated shunt tube 315 so as to allow for greater aqueous flow months or years after surgical implantation. In various embodiments, a plurality of reservoirs 320 can optionally be used.

In example embodiments, membrane 305 of GDDR 300 can comprise a divider (e.g., a divider 106 as shown in FIG. 1), which is configured to allow a medical practitioner to perforate specific areas selectively, and thereby selectively direct the flow of aqueous into one or more of a plurality of reservoirs 320. In other example embodiments, membrane 305 may comprise a continuous face, in which case the medical practitioner can still perforate specific areas selectively as described above to further reduce intraocular pressure, as desired.

By way of further illustration, and with continued reference to FIG. 3B, certain perforations in membrane 305 can open multi-lumen or bifurcated shunt tube 315A to allow the flow of aqueous into reservoir 320A, while other perforations in membrane 305 can open multi-lumen or bifurcated shunt tube 315B to allow the flow of aqueous into reservoir 320B. As above, the plurality of reservoirs 320 can be placed under the conjunctiva.

Figure 4:
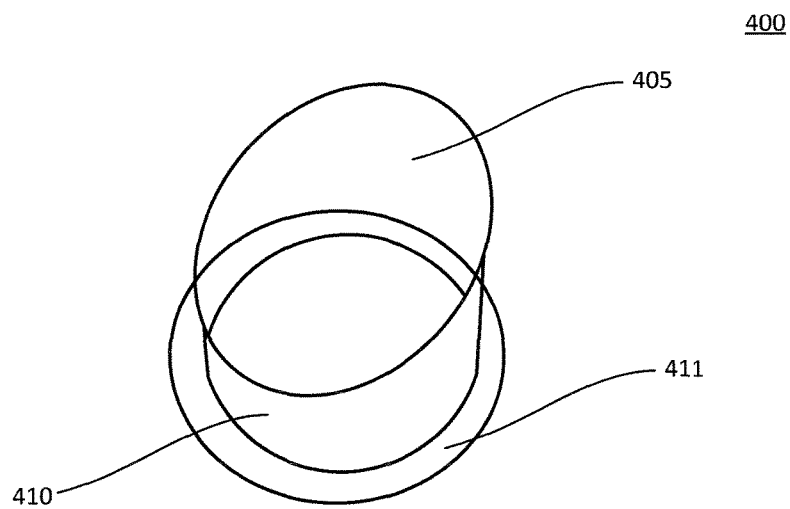
FIG. 4 illustrates a GDDR comprising a flange in accordance with an example embodiment of the present disclosure.

Turning now to FIG. 4, in connection with various embodiments, including those useful with trabeculectomy procedures, a GDDR 400 can further comprise a flange 411, e.g., for seating GDDR 400 at the sclerostomy in trabeculectomy surgery. In an example embodiment, flange 411 comprises a ring shape. In an example embodiment, flange 411 is circumferentially coupled with lumen 410. Flange 411 can be configured to circumferentially secure a lumen 410 and a membrane 405 on one or both opposing sides of one or more sclerostomy openings. In this regard, all or substantially all aqueous flowing through the sclerostomy opening(s) would flow through lumen 410 and membrane 405. More generally, flange 411 can be configured to secure lumen 410 and membrane 405 with respect to one or more sclerostomy openings, or within any other pathway for aqueous flow from an anterior chamber, and thereby direct flow through lumen 410 and membrane 405. As used herein, "pathway" refers to any naturally occurring or alternate, artificial pathway to drain aqueous from the anterior chamber of the eye.

Like lumen 410, flange 411 of GDDR 400 can be comprised of one or more biocompatible materials such as silicone, acrylic, PMMA, fluorinated ethylene propylene, stainless surgical steel, shape memory polymers, collamers, PVDF, and the like. Flange 411 may have holes which allow the passage of sutures or other materials to secure the implant to sclera or other tissue.

Figure 5:
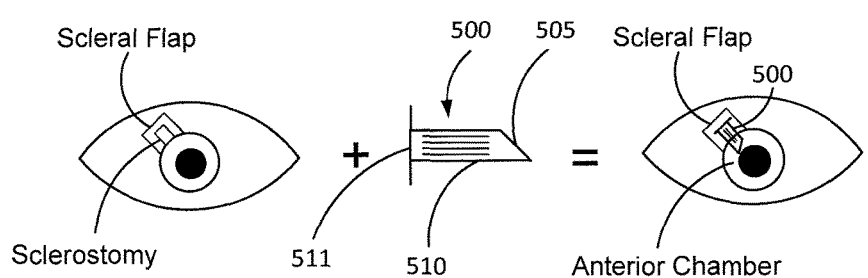
FIG. 5 illustrates progressive views of a GDDR comprising a flange implanted in connection with trabeculectomy in accordance with an example embodiment of the present disclosure.
Figure 6:
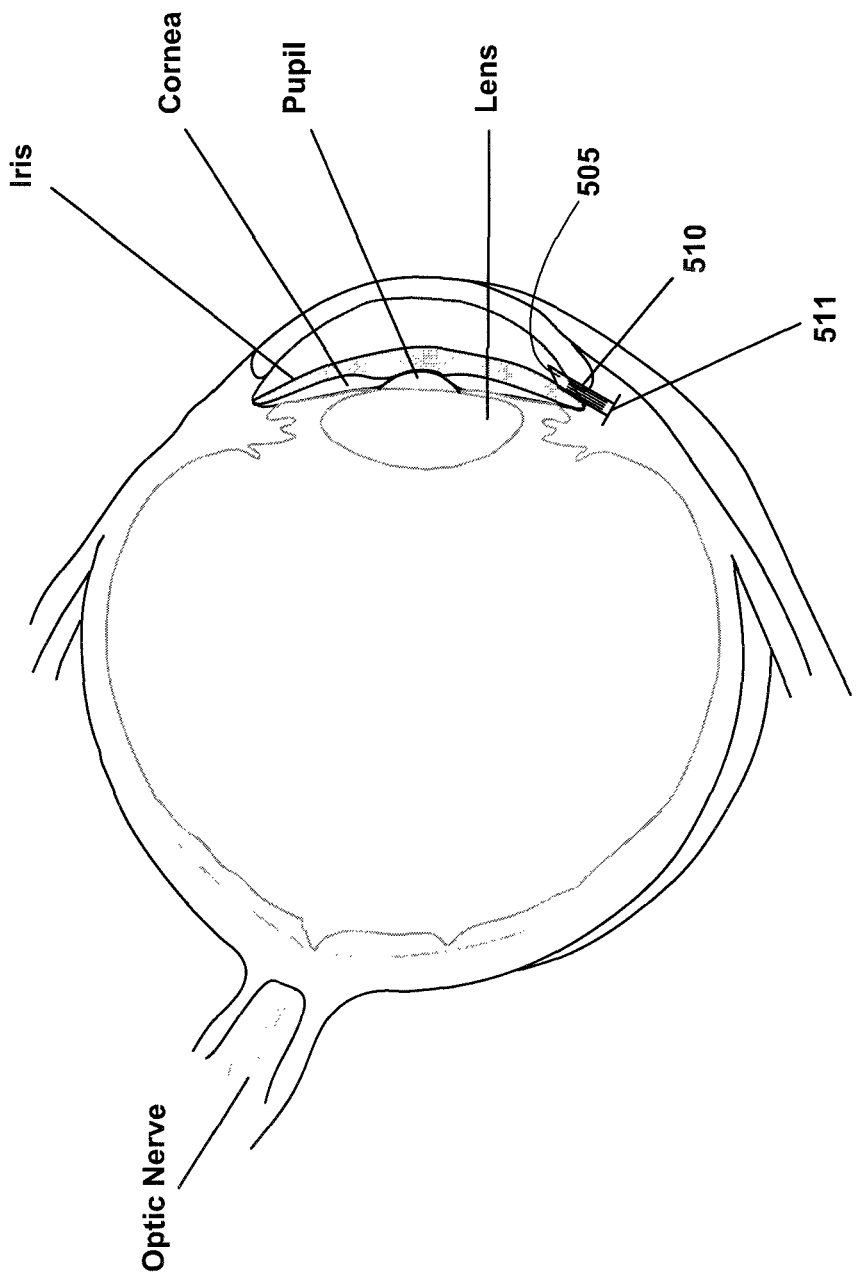
FIG. 6 illustrates an example GDDR in accordance with the present disclosure implanted in connection with trabeculectomy.

With reference to FIGS. 5 and 6, GDDR 500 comprising a lumen 510 and a flange 511 can be used in connection with trabeculectomy procedures by placing it beneath the scleral flap, through the sclerostomy with its tip into the anterior chamber. In such a configuration, membrane 505 will prevent aqueous flow until such time post-operatively that the medical practitioner determines the conjunctival wounds to be stable. Membrane 505 can then be perforated as clinical need dictates. Current trabeculectomy surgeries typically use a Kelley punch with an opening of 1-3 mm. In various embodiments, the present disclosure provides systems comprising one or more sclerostomy openings having smaller or larger diameters than those taught in the prior art. By way of non-limiting example, a larger diameter, for example 20 gauge or 18 gauge or greater, sclerostomy opening can be configured to allow for greater aqueous flow months or years after surgical implantation (e.g., when the patient's disease worsens) in cases where the high aqueous flow immediately post-operatively would be prohibitive. In this regard, one or more sclerostomy openings having smaller or larger diameters than those taught in the prior art, or multi-lumen or bifurcated sclerostomy openings can be implanted, and membrane 505 of GDDR 500 subsequently perforated as needed to increase the flow of aqueous into the one or more sclerostomy openings.

Stated another way, in an example embodiment, the sclerostomy opening inner diameter is configured to be greater than the maximum diameter that could be used on a patient at the time of operation if the operation was performed without the membrane of the present disclosure. Without the membrane of the present disclosure, a sclerostomy opening with too great an inner diameter would allow too much flow. In contrast, with the GDDR of the present disclosure, the sclerostomy opening inner diameter can be greater than the maximum diameter that could be used on a patient at the time of operation because the flow is restricted by membrane 505 in addition to the inner diameter of the sclerostomy opening. Moreover, the same sclerostomy opening can continue to be used at a subsequent time when additional perforation increases the flow of aqueous. Thus, subsequent adjustments can be made with minimal surgery impact on the patient.

Each of the membrane, lumen(s), shunt tube(s), reservoir(s), and flange can be temporarily or permanently coupled to one or more of the others by adhesion, compression fit, threading, suture, glue, thermal bonding, nitinol or other shape memory clips, and the like. Likewise, any plurality of the membrane, lumen(s), shunt tube(s), reservoir(s), and flange can be integral one with another. For example, in example embodiments, a membrane and a lumen comprise a single piece formed from a single mold, extruded together, etc. In example embodiments, a coupling is configured to maintain coupled elements firmly in place relative to one another even when subjected to shaking and acceleration/deceleration movements.

Illustrative methods for treating a patient having glaucoma, or otherwise lowering intraocular pressure, comprise implanting a GDDR as described supra within a pathway for aqueous flow from an anterior chamber, according to conventional surgical techniques for implanting a GDD, wherein perforations in a membrane of the GDDR increase aqueous flow to lower intraocular pressure within the anterior chamber. Illustrative methods can further comprise evaluating the patient's intraocular pressure at a later time (e.g., hours, days, weeks, months or years later), and further perforating the membrane as needed to further lower the patient's intraocular pressure.

Example embodiments further comprise decreasing the intraocular pressure within the anterior chamber by at least about 1%, more preferably at least about 5%, most preferably at least about 20%. Example embodiments further comprise decreasing the intraocular pressure within the anterior chamber by at least 1 mmHg, 2 mmHg, 4 mmHg or more, to at least about 16 mmHg, more preferably at least about 14 mmHg, most preferably about 10 mmHg, or an otherwise normal or improved intraocular pressure. Example embodiments still further comprise decreasing the intraocular pressure within the anterior chamber for at least about 2 weeks, or at least about 3-6 months, or at least about 1 year, 1 decade or more.

Figure 7:
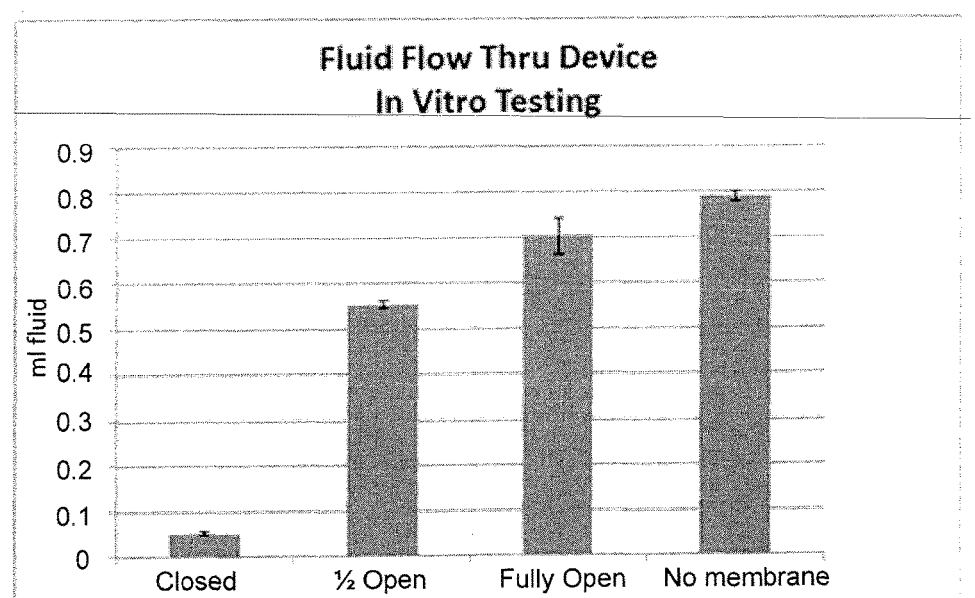
FIG. 7 illustrates in vitro test results in accordance with an example embodiment of the present disclosure.

The GDDR was tested in a model eye. The GDDR device was placed over the tip of a conventional GDD, and the tube placed into the model eye through a port. A second port was used to infuse fluid into the eye to maintain a physiologic pressure of 20 mmHg. The amount of fluid which passed through the tube was measured for 30 seconds. The membrane was placed initially with no laser perforations, then with enough laser to open half the membrane, and then more laser to open the membrane completely. Further, the tube was tested with no GDDR in place as a control. Three measurements were done for each configuration, and the results averaged. As shown in FIG. 7, increasing number of laser perforations allows for a titrable amount of flow through the tube of the GDD.

Figure 8:
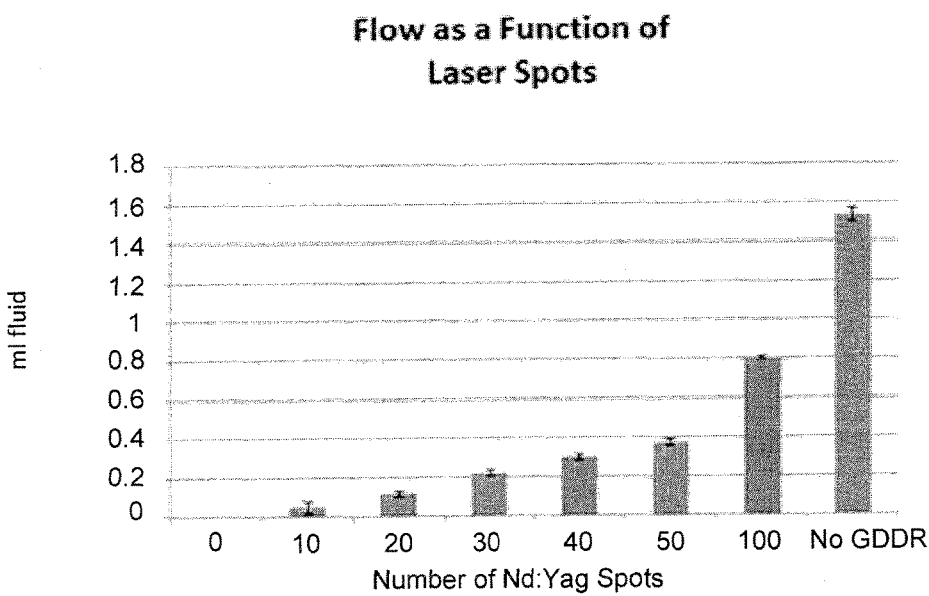
FIG. 8 illustrates ex-vivo test results in accordance with an example embodiment of the present disclosure.

The GDDR was tested ex-vivo in an enucleated porcine eye. The device was placed over the tip of a conventional GDD, and the tube placed into the eye through a corneal paracentisis. An infusion line was used to infuse saline into the eye to maintain a physiologic pressure of 20 mmHg. The amount of fluid which passed through the tube was measured for 60 seconds. The membrane was placed initially with no laser perforations, then with increasing amounts of laser to perforate the membrane, and then more laser to open the membrane completely. Further, the tube was tested with no GDDR in place as a control. Three measurements were done for each configuration, and the results averaged. As shown in FIG. 8, increasing number of laser perforations allows for a titrable amount of flow through the tube of the GDD.

In an example embodiment, a GDDR was configured to be compression fit over the top of a shunt tube. The GDDR was then subjected to stress testing. An example GDDR, composed of a 22 gauge silicone catheter with a 10 nm PVDF membrane, was placed over the tip of a standard 23 gauge silicone drainage tube from a GDD. The GDDR was easily placed on the tip using standard ophthalmic forceps. Once in place, the tube was subjected to shaking and acceleration/deceleration movements in an attempt to dislodge the GDDR. The GDDR remained firmly in place with the force of friction between its inner lumen and the outer lumen of the tube shunt.

As it relates to a further surgical technique using ex-vivo porcine eyes, the GDDR was placed over the tip of a standard tube shunt, which was then inserted into the anterior chamber of a porcine eye through a limbal paracentensis. With the GDDR in place, the tube passed easily through the wound and remained in place in the anterior chamber. Alternatively, the tube without the GDDR was first placed into the anterior chamber, and then the GDDR passed through the same wound in the anterior chamber. Conventional forceps were then used to place the GDDR on the tube of the GDD.

It will be apparent to those skilled in the art that various modifications and variations can be made in the present disclosure without departing from the spirit or scope of the disclosure. For example, while the moniker "glaucoma drainage device regulator" has been used in describing illustrative embodiments, the present disclosure is generally applicable to any treatment aimed at lowering intraocular pressure. Moreover, while example embodiments herein may have been described with reference to only one or the other of aqueous shunting and trabeculectomy procedures, such embodiments can be applied to the other, as well as to unnamed and yet undiscovered procedures. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A glaucoma drainage device regulator, comprising:
   a membrane coupled to an opening of a lumen,
   wherein the membrane is at an angle of about 30 to about 60 degrees to a longitudinal axis of the lumen,
   wherein the membrane is configured to be selectively perforated by a targeted energy source to form and define perforations,
   wherein the perforations defined in the membrane increase aqueous flow to lower intraocular pressure, and
   wherein the lumen of the glaucoma drainage device regulator is configured to be sealingly coupled around an end of a shunt tube.

2. The glaucoma drainage device regulator of claim 1, wherein the membrane is coupled to a shunt tube, wherein the angle between the membrane and a cornea of a patient is between about 30 degrees and about 60 degrees, wherein the angle facilitates formation of the perforations by a photodisruptive laser or an ablative laser.

3. The glaucoma drainage device regulator of claim 2, wherein the lumen is comprised of one or more of silicone, acrylic, PMMA, fluorinated ethylene propylene, stainless surgical steel, shape memory polymers, collamers and PVDF.

4. The glaucoma drainage device regulator of claim 1, wherein the membrane comprises at least one divider dividing the membrane into specific areas, wherein the specific areas are configured to be independently and selectively perforated.

5. The glaucoma drainage device regulator of claim 1, wherein the lumen is detachably coupled around the end of the shunt tube.

6. The glaucoma drainage device regulator of claim 1, wherein the membrane is comprised of PVDF or cellulose.

7. The glaucoma drainage device regulator of claim 6, wherein a surface of the membrane is color coded, numbered, or has writing or another target to indicate one or more areas to perforate.

8. A glaucoma drainage device regulator system, comprising:
   a membrane,
   a lumen coupled with the membrane, wherein the membrane is at an angle of about 30 to about 60 degrees to a longitudinal axis of the lumen,
   a shunt tube coupled with the lumen, and
   a reservoir coupled with the shunt tube,
   wherein the lumen is compression fit around an end of the shunt tube,
   wherein the membrane prevents aqueous flow,
   wherein the glaucoma drainage device regulator system is used in connection with aqueous shunting,
   wherein the membrane is configured to be selectively perforated by photodisruptive or ablative laser to form and define perforations, and
   wherein the perforations defined in the membrane increase aqueous flow to lower intraocular pressure.

9. The glaucoma drainage device regulator system of claim 8, wherein the lumen is comprised of one or more of silicone, acrylic, PMMA, fluorinated ethylene propylene, stainless surgical steel, shape memory polymers, collamers and PVDF.

10. The glaucoma drainage device regulator system of claim 8, wherein the membrane is comprised of PVDF or cellulose.

11. The glaucoma drainage device regulator system of claim 10, wherein a surface of the membrane is color coded, numbered, or has writing or another target to indicate one or more areas to perforate.

12. The glaucoma drainage device regulator system of claim 8, wherein the shunt tube comprises a plurality of lumens and a plurality of reservoirs, wherein the membrane comprises a divider that corresponds to the plurality of lumens, and wherein perforations in the membrane direct the flow of aqueous into only one of the plurality of reservoirs.

13. The glaucoma drainage device regulator system of claim 8, wherein the lumen is detachably coupled around the end of the shunt tube.

14. A method for regulating intraocular pressure, comprising:
providing a previously implanted shunt tube;
implanting a glaucoma drainage device regulator within a pathway for aqueous flow from an anterior chamber, wherein the glaucoma drainage device regulator comprises a membrane coupled to an end of a lumen, wherein the lumen is coupled as a cap around an end of the shunt tube, wherein the membrane is at an angle of about 30 to about 60 degrees to a longitudinal axis of the lumen;
selectively perforating the membrane using a targeted energy source to form and define perforations in the membrane to increase aqueous flow to lower an intraocular pressure within the anterior chamber, and wherein the membrane is configured to be selectively perforated by a targeted energy source;
evaluating the intraocular pressure at a time at least months later to determine if further perforating the membrane is needed to further lower the intraocular pressure.

15. The method of claim 14, wherein the lumen is configured to couple with a shunt tube and a reservoir, and wherein the method is used in connection with an aqueous shunting procedure.

16. The method of claim 14, wherein the step of providing a previously implanted shunt tube comprises providing a shunt tube implanted at least months previously.

17. The method of claim 14, further comprising a flange circumferentially coupled with the lumen, wherein the method is used in connection with a trabeculectomy procedure.

18. The method of claim 17, wherein the flange is comprised of one or more of silicone, acrylic, PMMA, fluorinated ethylene propylene, stainless surgical steel, shape memory polymers, collamers and PVDF.

19. The method of claim 14, wherein the membrane is comprised of PVDF or cellulose.

20. The method of claim 19, wherein a surface of the membrane is color coded, numbered, or has writing or another target to indicate one or more areas to perforate.

\* \* \* \* \*